United States Patent [19]

Smelser

[11] Patent Number: 4,821,714
[45] Date of Patent: Apr. 18, 1989

[54] PHARMACEUTICAL ENDOTRACHEAL TUBE

[76] Inventor: Danny N. Smelser, 205 Lincoln St., Florence, Ala. 35630

[21] Appl. No.: 937,679

[22] Filed: Dec. 4, 1986

[51] Int. Cl.$^4$ .................................... A61M 16/00
[52] U.S. Cl. ................... 128/207.14; 128/207.15; 604/27; 604/102
[58] Field of Search ............. 128/207.15, 207.14; 604/27, 36, 38, 102, 112, 181, 183, 187, 239, 240, 258, 280, 167

[56] References Cited

U.S. PATENT DOCUMENTS

| | | | |
|---|---|---|---|
| 2,493,326 | 1/1950 | Trinder | 128/342 |
| 3,313,299 | 4/1967 | Spademan | 604/167 |
| 4,327,721 | 5/1982 | Goldin et al. | 128/207.15 |
| 4,417,576 | 11/1983 | Baran | 128/207.15 |
| 4,423,725 | 1/1984 | Baran | 128/207.15 |
| 4,642,092 | 2/1987 | Moss | 604/280 |
| 4,669,463 | 6/1987 | McConnell | 128/207.14 |

Primary Examiner—Edward M. Coven
Assistant Examiner—J. P. Lacyk
Attorney, Agent, or Firm—C. A. Phillips

[57] ABSTRACT

An endotracheal device employing two or three integrated flexible tubes, a relatively large one and one or two smaller ones. One end of the larger tube is positioned in the trachea of a patient, and air or other breathable gas is administered through the other end, which end is external to the patient. One end of one of the smaller tubes is also positioned in the trachea, and this tube extends along the larger tube and terminates, external to the patient, in a puncturable membrane. This membrane is punctured by a hypodermic needle attached to a syringe containing a pharmaceutical fluid, and this fluid is pumped by the syringe through the small tube to the trachea. The fluid then passes into the lungs where it is absorbed into the patient's bloodstream. The second small tube, which is optional, depending upon the size of the endotracheal device, communicates with an inflatable cuff positioned in the trachea which, when inflated, "seals off" the trachea and helps maintain proper device positioning. The tube extends from the cuff, along the larger tube, and terminates, external to the patient, in a valvular apparatus through which air is pumped using a syringe, thus inflating the cuff.

15 Claims, 2 Drawing Sheets

PHARMACEUTICAL ENDOTRACHEAL TUBE

FIELD OF THE INVENTION

This invention relates generally to the administration of medicine to the pulmonary vasculature and is especially pertinent to the care of patients who have experienced cardiopulmonary arrest or have impending cardiopulmonary arrest, and in whom systemic vascular access is not immediately available. In particular, this invention relates to a method and apparatus for the pulmonary administration of phramaceuticals via an endotrachael tube designed to allow metered administration of drugs without necessitating the interruption of mechanical pulmonary ventilation.

BACKGROUND OF THE INVENTION

Cardiopulmonary arrest or impending cardiopulmonary arrest occurs commonly in hospital emergency departments and in prehospital settngs (ambulances, etc.). In such situations, it is routine for a physician, paramedic, or other qualified person to insert a breathing tube through the mouth or nose into the patient's trachea. Such a tube is called an "endotrachael tube." After an endotracheal tube is placed in the correct anatomical position, it may be attached to an oxygen source and mechanical ventilation performed. Typically, in such patients, mechanical ventilation with oxygen is in itself not sufficient to resuscitate successfully. Therefore, in addition to artificial ventilation, certain life-saving drugs may be necessary to help "restart" the heart. Such drugs are typically administered into the patient's bloodstream via an intravenous (IV) canula. Such canulas are placed in a systemic vein, such as an arm vein or large chest vein (in contrast to a pulmonary vessel). However, in recent years, it has been found that certain life-saving drugs, such as epinephrine, atropine, and lidocaine, also may be administered through the pulmonary (lung) vasculature. Patients receiving drugs via the pulmonary route have been documented to respond in a similar fashion as do those patients receiving drugs via systemic (arm or chest) administration. As a result of these discoveries, it is now the accepted standard practice to use the endotrachel route for life-saving drug administration if for some reason systemic venous access is not available. Since canulating a systemic vein is time-consuming or even impossible in many patients experiencing cardiopulmonary arrest, and since time is of the essence in administering life-saving drugs to these patients, the endotracheal route is often used during cardiopulmonary resuscitation. Currently, the accepted technique for administering endotracheal drugs involves the injection of the selected drug into the proximal end of the tube and then "blowing" the drug down the tube into the lungs. Deep in the lungs, the drug easily diffuses from the small air spaces (alveoli) through the air-blood membrane into the bloodstream.

With the current "state of the art" endotracheal tube, there are problems with administering endotracheal pharmaceuticals. Such problems are:

(1) interruption of artificial ventilation. In order to inject liquid medicine into the proximal end of an endotracheal tube, the mechanical breathing device must be removed, thus interrupting ventilation. There is no port in the endotracheal tube which is exclusively dedicated to drug administration.

(2) questionable delivery of drugs to the target tissue. Oftentimes during cardiopulmonary resuscitation, pulmonary secretions will collect in the endotracheal tube. When drugs are injected into the endotracheal tube, varying amounts of such drugs may be absorbed into thick secretions and be mechanically blocked from entering the lungs.

(3) questionable metering of endotracheal drugs. Even if the endotracheal tube is completely free of secretions, there is still the problem of metering the drug. Since the endotracheal tube has an extremely large diameter (usually seven to eight millimeters in adults, with decreasing dimensions corresponding to decreases in patient size) in relationship to the volume of fluid to be injected (usually five to ten millileters of fluid), a significant percentage of drug may adhere to the wall of the tube due to surface tension phenomena. Accordingly, the measure of drug injected into the proximal end of the endotracheal tube may not be the same measure which exits through the distal end of the tube and subsequently enters the pulmonary circulation.

Also the diameter-to-volume ratio makes a forcible, quick introduction of drug to the lung impossible. Rather, a drug is introduced into the endotracheal tube and then "blown" into the lungs when mechanical ventilation is reinstated.

Accordingly, it is the object of this invention to overcome the aforesaid problems and to provide an improved apparatus for and method of introduction of medication under emergency circumstances or where otherwise intravenous injection of medication is not feasible.

SUMMARY OF THE INVENTION

In accordance with this invention, an endotracheal device having one or more separate passageways, apart from an air passageway, is inserted into the trachea of the patient and held in place. A passageway is connected to a puncturable member, e.g., a diaphragm, and, with the endotracheal tube in place, medication is administered from a syringe with a hypodermic needle wherein first the needle of the syringe punctures the diaphragm, and then the syringe pump is operated to force medication through a discrete passageway or passageways and into the lungs in a single and immediate operation.

BRIEF DESCRIPTION OF THE DRAWINGS

FIG. 5 also illustrates the passageways for directing medicine into and out of the tube.

DESCRIPTION OF THE PREFERRED EMBODIMENTS

Figure 1:
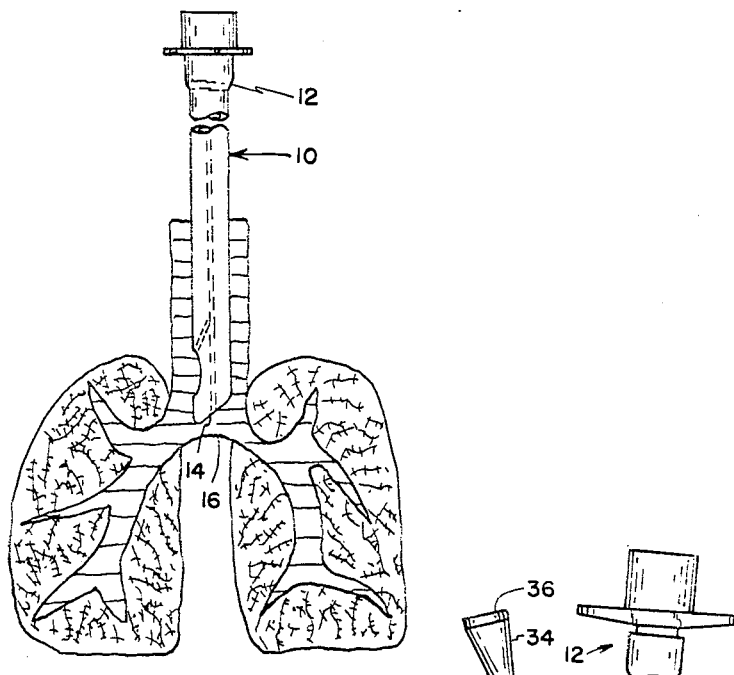
FIG. 1 is a pictorial illustration of an endotracheal tube inserted into the trachea and illustrating the passageways of one embodiment of the invention for administering medicine into the lungs of a patient.

As seen in FIG. 1, an endotracheal tube 10 is positioned in the trachea of a patient to aid the patient in breathing. Endotracheal tube 10 includes a proximal end 12 and a distal end 14. Proximal end 12 is open to outside air or to a ventillating machine. Distal end 14 is positioned in the trachea in proximity with the point 16 at which the trachea branches off into each lung.

Figure 4:
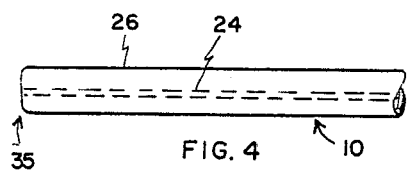
FIG. 4 is a view similar to FIG. 3 illustrating a single passageway and another type of tip of an endotracheal tube which has no side openings.
Figure 3:
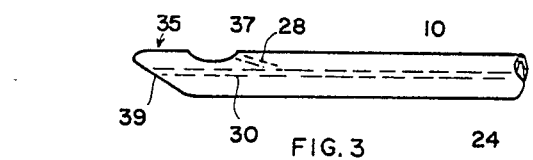
FIG. 3 is a partial top view taken along line 3—3 of FIG. 2 illustrating the paths of the passageways through which the medicine travels.
Figure 2:
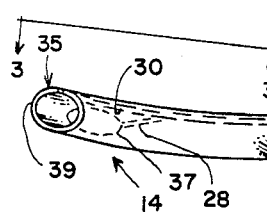
FIG. 2 is an elevational view illustrating an endotracheal tube having a single passageway which divides into two passageways for receiving and directing medicines out of the endotracheal tube and into the lungs of a patient.
Figure 2:
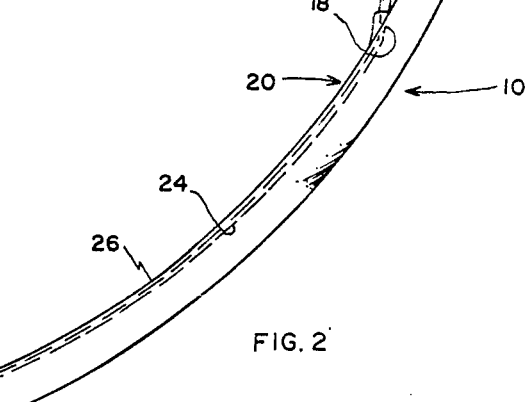

As seen in FIG. 2, the endotracheal tube is provided with an opening 18 in the side 20 thereof. A pharmaceutical tube 22 is secured in opening 18 in communication with a passageway 24 bored longitudinally through the wall 26 of the endotracheal tube. Near the distal end 14 of tube 10, passageway 24 branches out into two branches 28 and 30 (FIG. 3). Secured at the other (proximal) end 32 of tube 22 is a member 34 having a diaphragm 36 therein. The endotracheal tube shown in FIGS. 2, 3, 5, and 7 illustrates a Murphy tip 35 which includes side openings 37 and 39. However, it is to be understood that applicant's invention is not limited to use with only the Murphy tip and may be used with other tips, such as the Shiley tip, McGill tip, etc. FIG. 4 illustrates an endotracheal tube having a tip in which no side openings are provided and in which only a single passageway is used. However, if desired, more than one passageway may be used. However, it is desirable that the passageways terminate adjacent the distal end of the endotracheal tube and open exterior of the main passageway of the endotracheal tube. Further, as seen in FIG. 2, the tube is substantially straight and has no bends except for a typical slight bow between the ends thereof.

Some endotracheal tubes use a pneumatic tube 38 (FIG. 5) which connects into the body to inflate a pneumatic cuff 40 positioned adjacent distal end 14 of the tube. The pneumatic tube communicates into the wall 26 through an opening 42 and is sealed therein. Tube 38 communicates with a passage 44 bored longitudinally through wall 26. Passage 44 delivers air through openings 46 of wall 26 (positioned in the cuff) to inflate cuff 40 after the endotracheal tube is positioned in the trachea. Passage 44 terminates in the cuff. A valve 47 is provided at the other end 48 of the pneumatic tube for connection to a source of air (typically a plunger which is pushed into a cylinder to displace air therefrom into the pneumatic tube and cuff).

Figure 6:
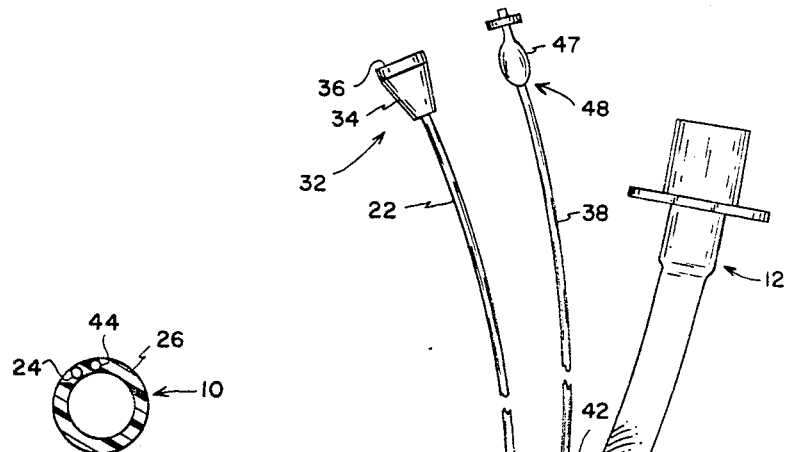
FIG. 6 is a sectional view taken along line 6—6 of FIG. 5.
Figure 5:
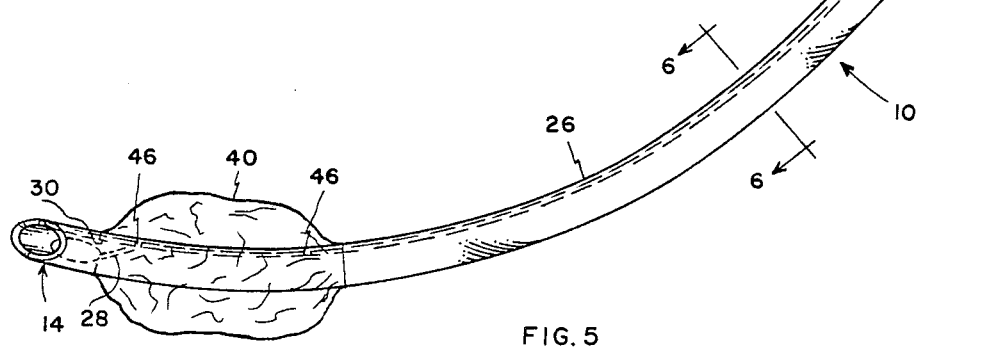
FIG. 5 is an elevational view of an endotracheal tube having a pneumatic cuff and passageways conecting the cuff to a pneumatic source.

In this type of endotracheal tube, pharmaceutical passageway 24 is bored in wall 26 and runs alongside bore 44 (FIG. 6) and branches out into branches 28 and 30, which terminate at the distal end 14 of tube 10. While a passageway having branches is described, it is to be understood that a single passage may be used, with the single passage terminating in the distal end of the endotracheal tube.

Figure 7:
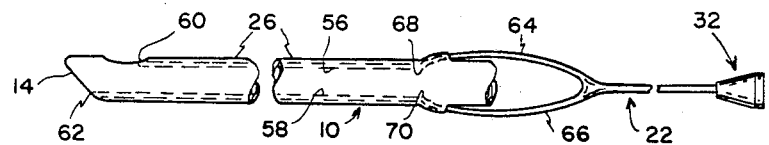
FIG. 7 is a plan view of an endotracheal tube having passageways on the opposite sides for directing medicine into the lungs of a patient.

Alternately, as shown in FIG. 7, a pair of passageways 56 and 58 may be bored on opposite sides of tube 10, through wall 26. The distal ends 60 and 62, respectively, terminate at the distal end 14 of tube 10 adjacent openings 60 and 62. Tubular member 22, in this case, branches out into branches 64 and 66 to communicate, respectively, with passageways 56 and 58, through openings 68 and 70. The branches 64 and 66 are sealed to wall 26 at their point of entry therethrough.

It is to be understood that where applicant refers to the pharmaceutical passageways in the endotracheal tube as being holes or channels bored in wall 26, tubular members running alongside the internal or external surface of the tube may be resorted to, if desired.

What is claimed is:

1. An endotracheal device coupleable to a syringe with a hypodermic needle comprising:
    a generally elongated, flexible, tubular member enclosing a main passageway and extending along the length thereof, said tubular member having a distal end positionable at the point where the trachea of a patient divides to form a passageway to each lung and having an opposite end configured for the introduction of a breathable gas;
    discrete tube means having a termination end adjacent the distal end of said tubular member, said discrete tube means extending along said tubular member for a discrete distance and then separating from said tubular member and ending in a second opening end;
    puncturable closure means secured to said second end of said discrete tube means; and
    said discrete tube means being of smaller diameter than said tubular member;
    whereby, while applying a breathable gas through said opposite end of said tubular member, puncturing said puncturable closure means with the needle end of said hypodermic syringe having a pharmaceutical fluid therein and effecting a pumping action on said syringe, said pharmaceutical is positively forced through said discrete tube means and out said termination end into the lungs of a patient and therefrom absorbed through the walls of the lungs of a patient into the bloodstream of a patient.

2. An endotracheal device as set forth in claim 1 wherein said termination end includes an exit end region comprising a pair of branched passageways terminating on opposite sides of said tubular member, whereby, responsive to the pumping of a pharmaceutical fluid into said discrete tube means, said pharmaceutical fluid flows toward the right and left main stem bronchi, respectively, in a directed fashion.

3. An endotracheal device as set forth in claim 1 wherein said discrete tube means is a single tube positioned within the outer surface of said tubular member.

4. An endotracheal device as set forth in claim 1 wherein said discrete tube means is a single tube formed in the wall of said tubular member.

5. An endotracheal device as set forth in claim 1 including:
    an inflatable cuff positioned around said tubular member intermediate the ends thereof and a second discrete tube having one end communicating with said cuff, and then said second tube extending along said tubular member for a discrete distance and then separating from said tubular member; and
    cuff inflation means coupled to an opposite end of said tube for applying air pressure to said cuff and thereby effecting a holding action on said cuff by engagement of said cuff with a patient.

6. An endotracheal device as set forth in claim 2 wherein said discrete tube means is a single tube positioned within the outer surface of said tubular member.

7. An endotracheal device as set forth in claim 2 wherein said discrete tube means is a single tube formed in the wall of said tubular member.

8. An endotracheal device as set forth in claim 2 including:
   an inflatable cuff positioned around said tubular member intermediate the ends thereof and a second discrete tube having one end communicating with said cuff, and then said second tube extending along said tubular member for a discrete distance and then separating from said tubular member; and
   cuff inflation means coupled to an opposite end of said tube for applying air pressure to said cuff and thereby effecting a holding action on said cuff by engagement of said cuff with a patient.

9. An endotracheal device as set forth in claim 1 wherein said discrete tube means includes a pair of discrete tubes, each positioned on opposite sides of said endotracheal tube, said pair of discrete tubes merging into a single tube terminating at said diaphragm closure means.

10. An endotracheal device as set forth in claim 9 wherein said pair of tubes is positioned within the outer surface of said tubular member.

11. An endotracheal device as set forth in claim 9 wherein said pair of tubes is formed in the wall of said tubular member.

12. An endotracheal device as set forth in claim 9 including:
   an inflatable cuff positioned around said tubular member intermediate the ends thereof and a second discrete tube having one end communicating with said cuff, and then said second tube extending along said tubular member for a discrete distance and then separating from said tubular member; and
   cuff inflation means coupled to an opposite end of said tube for applying air pressure to said cuff and thereby effecting a holding action on said cuff by engagement of said cuff with a patient.

13. An endotracheal device coupleable to a syringe with a hypodermic needle comprising:
   a generally elongated, flexible, tubular member enclosing a main passageway and extending along the length thereof, said tubular member having a distal end positionable at the point where the trachea of a patient divides to form a passageway to each lung and having an opposite end configured for the introduction of a breathable gas;
   discrete tube means having a termination end adjacent the distal end of said tubular member, said termination end of said discrete tube means opening exterior to said main passageway, and said discrete tube means extending along said tubular member for a discrete distance and then separating from said tubular member and ending in a second opening end;
   puncturable closure means secured to said second end of said discrete tube means; and
   said discrete tube means being of smaller diameter than said tubular member;
   whereby, while applying a breathable gas through said opposite end of said tubular member, puncturing said puncturable closure means with the needle end of said hypodermic syringe having a pharmaceutical fluid therein and effecting a pumping action on said syringe, said pharmaceutical is positively forced through said discrete tube means and out said termination end into the lungs of a patient and therefrom absorbed through the walls of the lungs of a patient into the bloodstream of a patient.

14. A method of administering medicine to the lungs of a patient comprising:
   placing an endotracheal device through the trachea of a patient wherein:
   said device comprises a generally elongated tubular assembly,
   said assembly includes an elongated, flexible, tubular member having a distal end positioned at the point where the trachea divides to form a passageway to each lung, and having an opposite end configured for introduction of a breathable gas,
   said device further including a discrete tube having a termination end adjacent the distal end of said tubular member and extending along said tubular member for a discrete distance and then separating from said tubular member, and said discrete tube having a second end provided with a diaphragm secured thereto,
   said discrete tube being of smaller diameter than said tubular member, and
   while applying a breathable gas through an opposite end of said tubular member, puncturing said diaphragm with the needle end of a hypodermic syringe having a pharmaceutical fluid therein and effecting a pumping action on said syringe and thereby positively forcing said pharmaceutical fluid through said discrete tube and out said termination end into the lungs of a patient.

15. A method of administering medicine as set forth in claim 14 wherein said device further includes an inflatable cuff positioned around said tubular member intermediate the ends thereof and a second discrete tube extending from said cuff along said tubular member and separating from said tubular member a substantial distance along said tubular member from said cuff, and cuff inflation means is connected to an end of said second tube opposite said cuff.

* * * * *